(12) United States Patent
Takahashi et al.

(10) Patent No.: US 7,622,026 B2
(45) Date of Patent: Nov. 24, 2009

(54) BIOSENSOR

(75) Inventors: Koji Takahashi, Matsuyama (JP);
Akihisa Higashihara, Touon (JP)

(73) Assignee: Panasonic Corporation, Osaka (JP)

( * ) Notice: Subject to any disclaimer, the term of this patent is extended or adjusted under 35 U.S.C. 154(b) by 864 days.

(21) Appl. No.: 11/067,889

(22) Filed: Mar. 1, 2005

(65) Prior Publication Data

US 2005/0239194 A1 Oct. 27, 2005

(30) Foreign Application Priority Data

Mar. 2, 2004 (JP) .............................. 2004-058017
Mar. 24, 2004 (JP) .............................. 2004-086021

(51) Int. Cl.
*G01N 27/327* (2006.01)

(52) U.S. Cl. ................................ 204/403.02; 204/403.1

(58) Field of Classification Search ............ 204/403.01, 204/403.02, 403.1; 205/777.5, 778, 792
See application file for complete search history.

(56) References Cited

U.S. PATENT DOCUMENTS

| 2002/0148726 | A1* | 10/2002 | Yamamoto et al. | ..... 204/403.14 |
| 2003/0175946 | A1 | 9/2003 | Tokunaga et al. | |
| 2004/0043477 | A1 | 3/2004 | Schibli | |
| 2004/0178066 | A1 | 9/2004 | Miyazaki et al. | |

FOREIGN PATENT DOCUMENTS

| CN | 1439058 | 8/2003 |
| CN | 1461410 | 12/2003 |
| EP | 1152239 | 11/2001 |
| JP | 1-321087 | 12/1989 |
| JP | 2000-317663 | 11/2000 |
| JP | 2003-501626 | 1/2003 |
| WO | 00/73778 | 12/2000 |
| WO | 01/36953 | 5/2001 |

* cited by examiner

*Primary Examiner*—Kaj K Olsen
(74) *Attorney, Agent, or Firm*—Wenderoth, Lind & Ponack, L.L.P.

(57) ABSTRACT

There is provided a biosensor in which a spacer 6 having a cutout portion is bonded between at least first support 1 and a second support 8 to form a specimen supply path 7 through which a supplied specimen is sucked into a space between the supports 1 and 8, a reagent that reacts with a component in the specimen is placed in the specimen supply path 7, and an air hole 9 for promoting suction of the specimen is formed in the second support; wherein the air hole 9 is shaped such that a diameter y of an opening 91*b* at one surface of the second support 8 which faces the specimen supply path 7 is larger than a diameter x of an opening 91*a* at the other surface of the second support, and projecting parts 92*a* and 92*b* are formed at the peripheries of the openings 91*a* and 91*b*, respectively. Thereby, a sufficient amount of specimen can be sucked regardless of the viscosity of the specimen supplied to the biosensor, and further, the specimen is prevented from flowing over the air hole 9.

12 Claims, 5 Drawing Sheets

Prior Art

Prior Art

BIOSENSOR

FIELD OF THE INVENTION

The present invention relates to a compact and disposable biosensor which can analyze a specific component in a liquid sample by utilizing a reaction between the liquid sample and a reagent and, more particularly, to a biosensor which can provide a highly precise measurement result.

BACKGROUND OF THE INVENTION

A biosensor is a sensor which utilizes a molecule recognizing ability of a biological material such as micro-organisms, enzymes, antibodies, DNA, RNA and the like, and applies a biological material as a molecule recognition element. To be specific, it utilizes a reaction which is caused when an immobilized biological material recognizes an objective substrate, such as enzyme consumption due to respiration of a micro-organism, enzyme reaction, light emission, and the like. Among various biosensors, an enzyme sensor has progressively come into practical use, and an enzyme sensor for glucose, lactic acid, uric acid, and amino acid, has been utilized in medical diagnostics or food industry.

For example, this enzyme sensor reduces an electron acceptor by an electron which is generated by a reaction of substrate included in a sample liquid as a specimen and enzyme or the like, and a measurement apparatus electrochemically measures a reduction quantity of the electron acceptor, thereby performing quantitative analysis of the specimen (for example, refer to the brochure of international publication No. 01/36953).

Figure 6A:
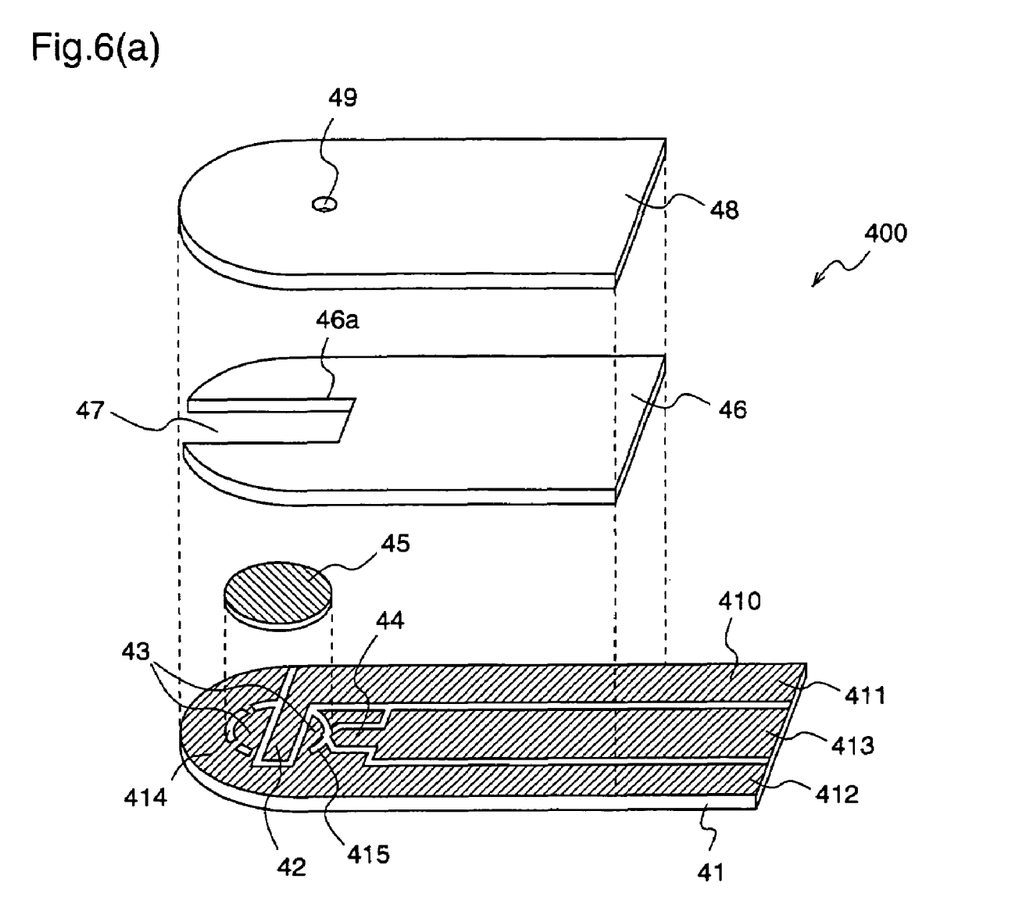
FIGS. 6(a) and 6(b) are an exploded perspective view and a plan view, respectively, illustrating the construction of the conventional biosensor.

Hereinafter, a conventional biosensor will be described with reference to FIGS. 6 and 7. FIG. 6(a) is an exploded perspective view illustrating the structure of the biosensor, and FIG. 6(b) is a plan view of the biosensor shown in FIG. 6(a).

Figure 6B:
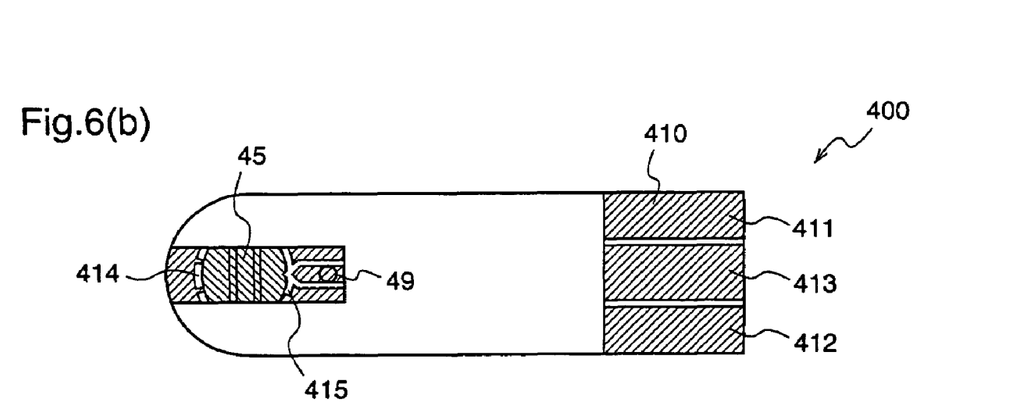

With reference to FIGS. 6(a) and 6(b), a biosensor 400 is composed of a first insulating support (hereinafter referred to as "first support") 41 comprising polyethylene terephthalate or the like, a reagent layer 45, a spacer 46 having a cutout part 46a for forming a specimen supply path 47, and a second insulating support (hereinafter referred to as "second support") 48 having an air hole 49. The spacer 46 and the reagent layer 45 are sandwiched between the first support 41 and the second support 48 to be integrally arranged.

A conductive layer 410 comprising an electrical conductive material such as a noble metal, e.g., gold or palladium, or carbon is formed on the surface of the first support 41 by employing a screen printing method, a sputtering evaporation method, or the like. The conductive layer 410 on the first support 41 is divided by plural slits, thereby providing a measurement electrode (hereinafter also referred to as "working electrode") 42, a counter electrode 43, a detection electrode 44, and nearly arc shaped slits 414 and 415. Reference numerals 411, 412, and 413 are terminals of the measurement electrode 42, the counter electrode 43, and the detection electrode 44, respectively.

A reagent including enzyme, electron carrier, water-soluble polymer and the like, which uniquely reacts with a specific component in a sample liquid, is applied to the electrodes 42, 43, and 44, thereby forming the reagent layer 45, and spread of the reagent applied onto the electrodes 42, 43, and 44 is restricted by the nearly arc shaped slits 414 and 415 formed in the counter electrode 43.

The spacer 46 is further laminated thereon, and the specimen supply path 47 is formed by the rectangle cutout part 46a that is provided in the center of the front edge of the spacer 46.

The second support 48 is laminated and bonded onto the spacer 46 so that an end of the cutout part 46a of the spacer 46 leads to the air hole 49 provided in the second support 48.

Hereinafter, a description will be given of the procedure for measuring the content of the substrate in the sample liquid (specimen) using the conventional biosensor 400 constituted as described above.

Initially, a measurement apparatus (not shown) is connected to the biosensor 400, and a fixed voltage is applied to a space between the counter electrode 43 or the measurement electrode 42 and the detection electrode 44 by the measurement apparatus. Then, the sample liquid is supplied to the inlet of the specimen supply path 47 with the voltage being applied to the space between the two electrodes of the biosensor 400. The supplied sample liquid is drawn inside the specimen supply path 47 by capillary phenomenon, and passes on the counter electrode 43 and the measurement electrode 42 to reach the detection electrode 44. The sample liquid that has reached the detection electrode 44 dissolves the reagent layer 45. The measurement apparatus detects an electrical change that occurs between the counter electrode 43 or the measurement electrode 42 and the detection electrode 44, and starts a measurement operation.

In the above-described biosensor, at least two supports, i.e., the first and second supports 41 and 48 are bonded together to form the specimen supply path 47 through which the specimen is drawn into a space between the supports, and the reagent for analyzing the components of the drawn specimen is placed in the specimen supply path 47, and further, the air hole 49 that leads from the specimen supply path 47 to the outside is formed in at least one of the supports. When forming the air hole 49, in the conventional method, a portion of the second support is punched out by press working to open a hole having openings with flat peripheries as shown in FIGS. 7(a) and 7(b).

Figure 7A:
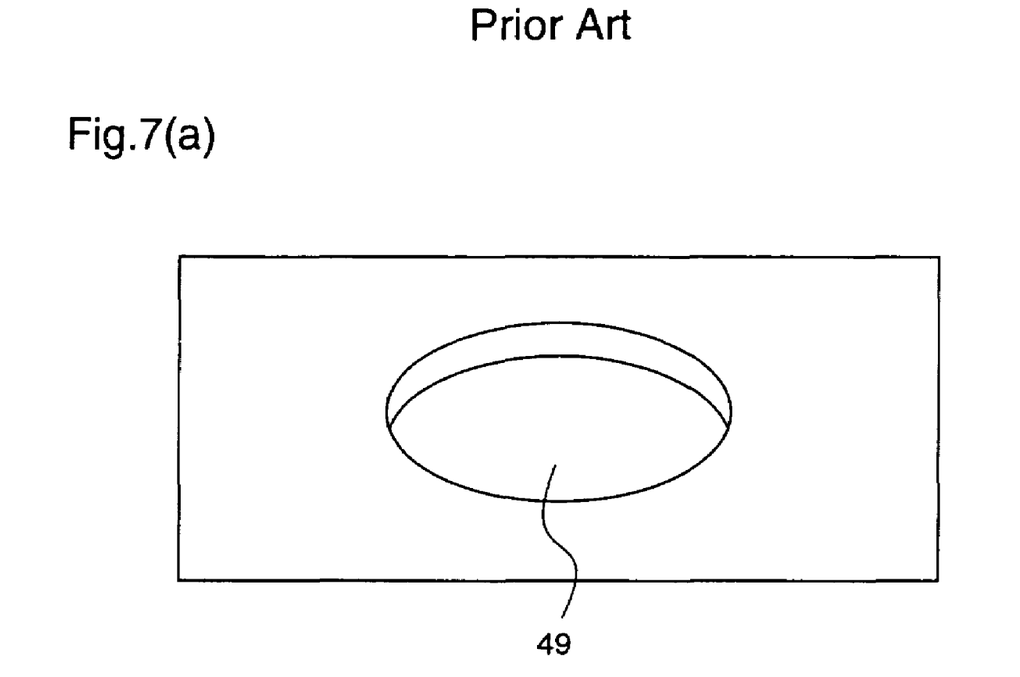
FIGS. 7(a) and 7(b) are a perspective view and a cross-sectional view, respectively, illustrating the shape of an air hole formed by the conventional press working.
Figure 7B:
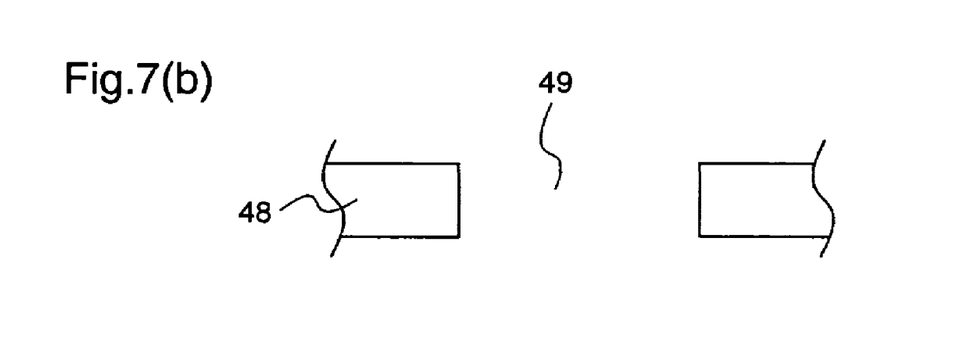

FIG. 7(a) is a perspective view illustrating the shape of the air hole that is produced by the conventional press working, and FIG. 7(b) is a cross-sectional view of the air hole.

In recent years, however, there has been a demand for a reduction in the amount of blood as a specimen to be supplied to the biosensor 400. With this demand, the size of the specimen supply path 47 is reduced, and consequently, the size of the air hole 49 formed in the second support 48 must be reduced.

However, reducing the size of the air hole 49 when it is formed by the press working causes a residue of the second support 48 that stays in the air hole 49 although a hole can be formed by pressing the second support 48. If a biosensor with the residue remaining in the air hole 49 is produced, a sufficient amount of specimen supplied cannot be drawn in the biosensor, resulting in a problem relating to measurement precision. The minimum diameter of the air hole which can be formed by the press working without the above-mentioned problem is 0.3 mm. Considering productivity, the diameter of the air hole by the current press working is 0.35 mm.

As a countermeasure against the above-mentioned problem, it is considered that a minute hole is formed not by pressing the second support 48 but by thermally melting the second support 48 with a laser or the like. According to this method, in contrast to the press working, no residue remains in the air hole 49, and further, a minute air hole can be formed.

However, when the size of the air hole to be formed in the second support 48 using the laser processing is too small, if the specimen supplied to the biosensor is a control solution or the like having a relatively low viscosity, since the speed at which the specimen is drawn into the specimen supply path 7 is too high as compared with the speed at which the air collected in the specimen supply path 47 gets out of the air hole 49, air bubbles remain in the specimen supply path 47 and thereby a sufficient amount of specimen cannot be drawn, resulting in a new problem that accurate measurement result cannot be obtained, although there occurs no problem when the specimen supplied to the biosensor is blood or the like having a relatively high viscosity.

Further, in the conventional biosensor 400 having the construction as described above, when a minute air hole 49 is formed and a specimen having a significantly low viscosity or a control solution is supplied to the air hole so as to be drawn into the specimen supply path 47, the supplied specimen as well as the dissolved reagent flow out of the air hole 49, whereby the measurement value to be detected by the measurement apparatus is lowered, resulting in a problem that highly accurate measurement value cannot be obtained.

In order to solve this problem, for example, it is considered that the surface of the second support 48 is coated with a water-shedding resin such as silicon to prevent the liquid specimen from flowing over the air hole 49.

However, prevention of overflow of the liquid specimen from the air hole 49 by the above-mentioned method takes much time and cost for applying the water-shedding material on the second support 48.

SUMMARY OF THE INVENTION

The present invention is made to solve the above-mentioned problems and has for its object to provide a biosensor which can suck a sufficient quantity of specimen regardless of the viscosity of the supplied specimen, and is provided with a minute air hole from which the specimen does not overflow.

In order to solve the above-mentioned problems, according to a first aspect of the present invention, there is provided a biosensor in which at least first and second supports are bonded together to make a specimen supply path through which a supplied specimen is sucked into a space between the supports, a reagent which reacts with a component of the specimen is disposed in the specimen supply path, and an air hole which leads from the specimen supply path to the outside is formed in the second support; wherein a diameter of an opening of the air hole at one surface of the second support which faces the specimen supply path is larger than a diameter of an opening of the air hole at the other surface of the second support.

Therefore, even if the air hole perforated by perforating the second support is minute, releasing of air from the specimen supply path is promoted, whereby a sufficient amount of specimen can be sucked regardless of the viscosity of the supplied specimen.

According to a second aspect of the present invention, in the biosensor according to the first aspect, the area of the opening at the one surface of the second support facing the specimen supply path is $1.76 \times 10^{-2} \sim 3.14 \times 10^{-2}$ mm$^2$, and the area of the opening at the other surface of the second support is $1.96 \times 10^{-3} \sim 7.85 \times 10^{-3}$ mm$^2$.

Therefore, even if the air hole formed by perforating the second support is minute, releasing of air from the specimen supply path is promoted, whereby a sufficient amount of specimen can be sucked regardless of the viscosity of the supplied specimen.

According to a third aspect of the present invention, in the biosensor according to the first aspect, the openings of the air hole are nearly circular in shape, and the diameter of the opening at the one surface of the second support facing the specimen supply path is 0.15~0.20 mm, and the diameter of the opening at the other surface of the second support is 0.05~0.10 mm.

Therefore, even if the air hole is minute, releasing of air from the specimen supply path can be promoted, whereby a sufficient amount of specimen can be sucked regardless of the viscosity of the supplied specimen.

According to a fourth aspect of the present invention, in the biosensor according to the first aspect, the air hole has a first projecting part that is formed on the periphery of the opening at the other surface of the second support, and a second projecting part that is formed on the periphery of the opening at the one surface of the second support facing the specimen supply path.

Therefore, overflow of the specimen from the air hole can be prevented regardless of the viscosity of the supplied specimen.

According to a fifth aspect of the present invention, in the biosensor according to the fourth aspect, when the thickness of the second support is 0.01 mm~0.5 mm and the area of the opening at the other surface of the second support is $1.96 \times 10^{-3} \sim 7.85 \times 10^{-3}$ mm$^2$, the heights of the first and second projecting parts are 0.005~0.04 mm.

Therefore, even if the air hole is minute, overflow of the specimen from the air hole can be prevented regardless of the viscosity of the supplied specimen.

According to a sixth aspect of the present invention, in the biosensor according to the fourth aspect, the height of the first projecting part is larger than the height of the second projecting part.

Therefore, overflow of the specimen from the air hole can be prevented regardless of the viscosity of the supplied specimen, and releasing of air from the specimen supply path can be promoted.

According to a seventh aspect of the present invention, in the biosensor according to the first aspect, the air hole is formed by perforating the second support with laser irradiation.

Therefore, a minute air hole can be easily perforated in the second support, and further, no residue remains when the second support is perforated.

According to an eighth aspect of the present invention, in the biosensor according to the first aspect, the shape of the opening of the air hole is any of circle, ellipse, line having a very small width, triangle, square, rectangle, and polygon.

BEST MODE TO EXECUTE THE INVENTION

Embodiment 1

Figure 1A:
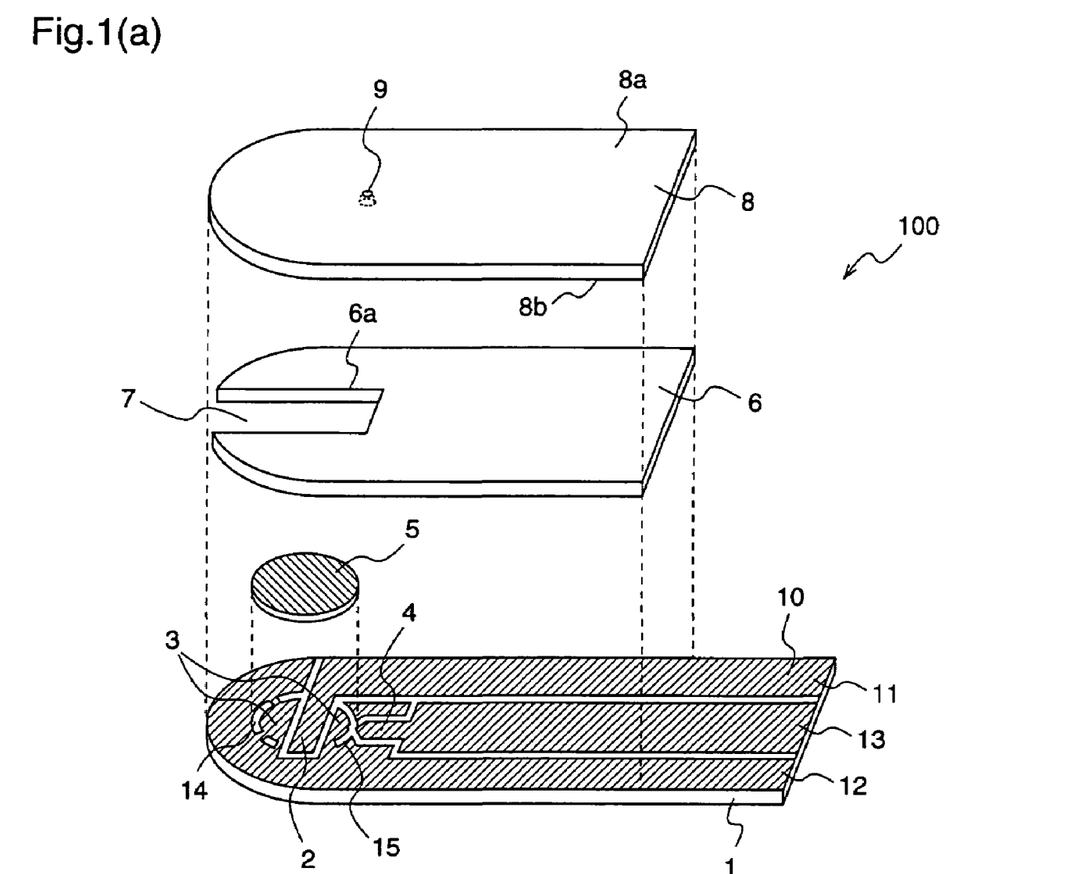
FIGS. 1(a) and 1(b) are an exploded perspective view and a plan view, respectively, illustrating the construction of a biosensor according to a first embodiment of the present invention.

Hereinafter, a biosensor 100 according to a first embodiment of the present invention will be described with reference to the drawings. FIG. 1(a) is an exploded perspective view of a biosensor, and FIG. 1(b) is a plan view of the biosensor shown in FIG. 1(a).

Figure 1B:
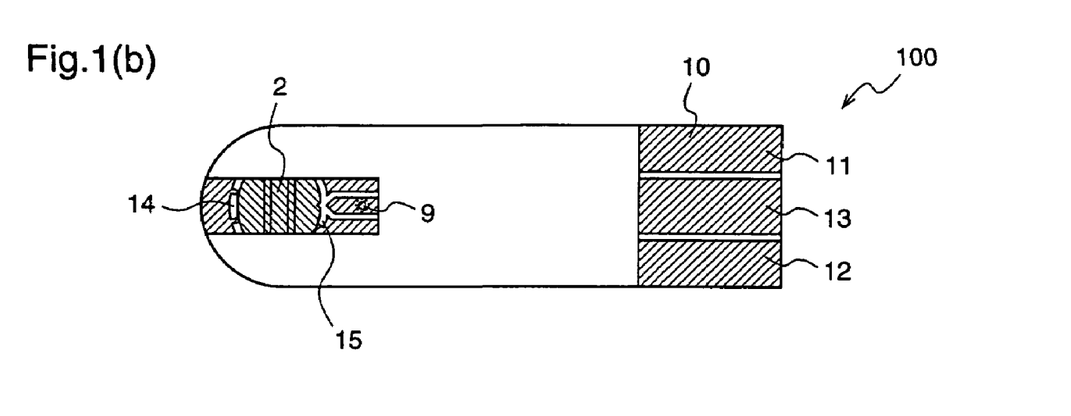

With reference to FIGS. 1(a) and 1(b), reference numeral 1 denotes a first insulating support (hereinafter referred to as "first support") comprising polyethylene terephthalate or the like, and a conductive layer 10 comprising an electrical conductive material such as a noble metal (e.g., gold or palladium) or carbon is formed on the surface of the first support 1 by screen printing, sputtering evaporation, or the like. The conductive layer 10 is formed over the entire surface or at least a part of the first support 1.

On the first support 1, the conductive layer 10 is divided by plural slits, thereby providing a counter electrode 3, a measurement electrode 2, a detection electrode 4, and reagent overflow prevention lines 14 and 15.

Reference numeral 8 denotes a second insulating support (hereinafter referred to as "second support") on which an approximately circular air hole 9 is formed in a center region, and the second support 8 preferably comprises a plastic film such as polyester, polyolefin, polyamide, polyether, polyamide-imide, polystyrene, polycarbonate, poly-ρ-phenylene sulfide, polyvinylchloride. Further, the second support 8 may comprise a copolymer, or blend, or cross-linkage of these materials, and its thickness is 0.01 mm~0.5 mm.

A spacer 6 having a cutout part 6a which provides a specimen supply path 7 for supplying a specimen into the biosensor 100, and a reagent layer 5 impregnated with a reagent are sandwiched between the second support 8 and the first support 1, and thereby the second support 8 is integrated with the first support 1.

The cutout part 6a of the spacer 6 is formed by cutting out a rectangle center portion of the front end of the spacer 6, and the spacer 6 having the cutout part 6a is placed so as to cover the counter electrode 3, the measurement electrode 2, and the detection electrode 4 on the first support 1, whereby the specimen supply path 7 is formed. The reagent layer 5 is formed by applying a reagent containing enzyme, electron acceptor, amino acid, sugar alcohol and the like onto the counter electrode 3, the measurement electrode 2, and the detection electrode 4 which are exposed at the cutout part 6a of the spacer 6. In FIG. 1(a), 11, 12, and 13 denote the terminals of the counter electrode 3, the measurement electrode 2, and the detection electrode 4, respectively.

Hereinafter, the air hole 9 formed in the second support 8 will be described in detail.

The air hole 9 of the first embodiment is formed by perforating the second support 8 using laser. When perforating the air hole 9 using laser as described above, a desired size of the air hole can be obtained by changing the laser condition or the irradiation condition. For example, the diameter of the air hole 9 can be increased by increasing the diameter of the irradiating laser beam, the laser power, or the laser irradiating time.

Figures 2A, 2B:
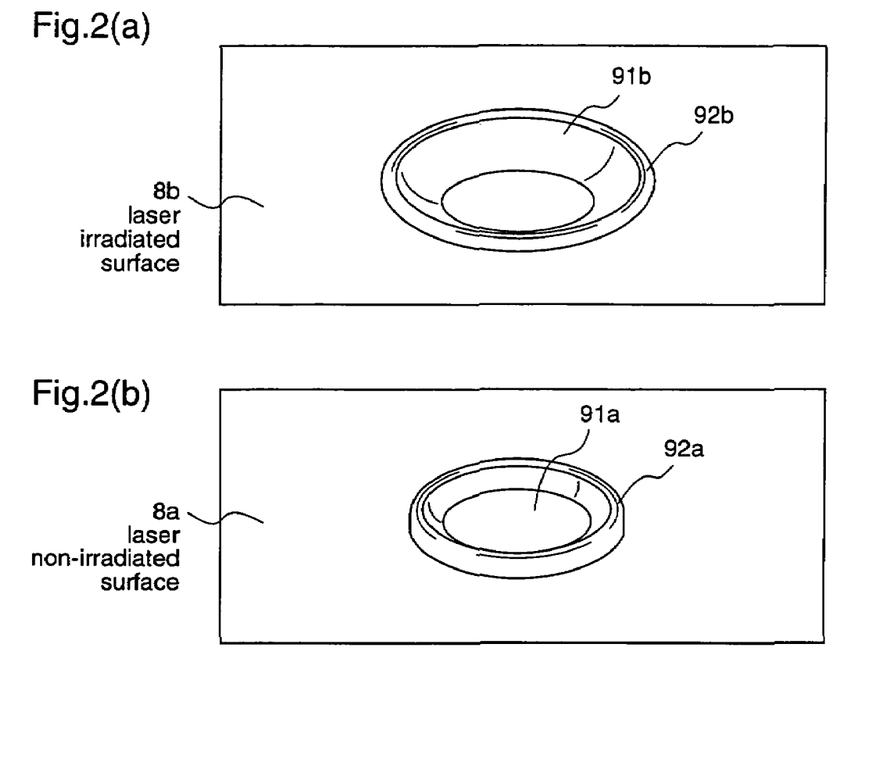
FIGS. 2(a) and 2(b) are perspective views illustrating the shapes of laser opening parts of an air hole according to the first embodiment of the invention, wherein 2(a) shows a laser irradiated surface side and 2(b) shows the laser non-irradiated surface side.
Figure 3:
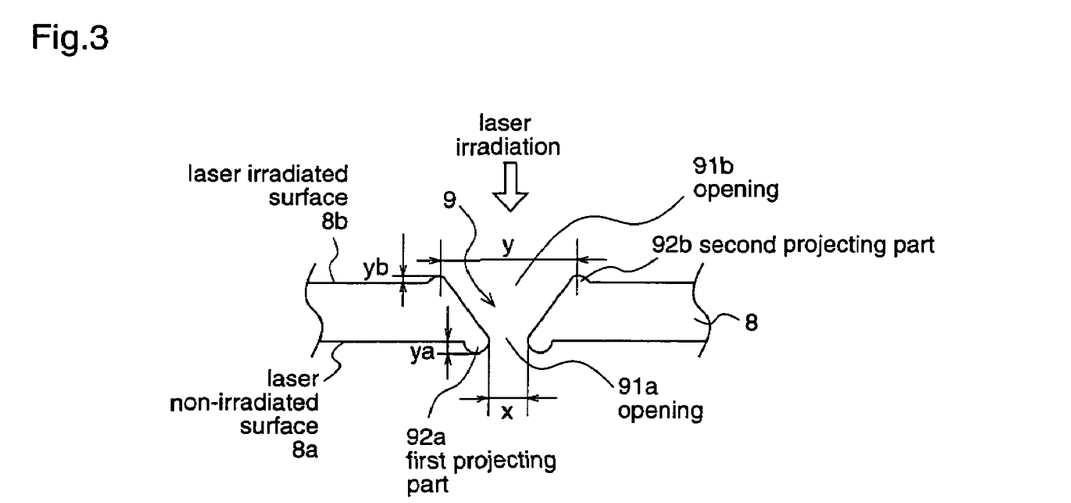
FIG. 3 is a cross-sectional view of the air hole according to the first embodiment of the present invention.

FIGS. 2(a) and 2(b) are diagrams illustrating the shape of the air hole that is formed by perforating the second support using $CO_2$ laser processing. Specifically, FIG. 2(a) is a perspective view of the air hole viewed from the $CO_2$ laser irradiated surface 8b side, and FIG. 2(b) is a perspective view of the air hole viewed from the $CO_2$ laser non-irradiated surface 8a side. Further, FIG. 3 is a cross-sectional view of the air hole shown in FIG. 2. In these figures, reference numeral 91a denotes an opening on the $CO_2$ laser non-irradiated surface 8a side, 92a denotes a projecting part that is formed at the periphery of the opening on the laser non-irradiated surface 8a side (hereinafter referred to as "first projecting part"), 91b denotes an opening on the $CO_2$ laser irradiated surface 8b side, and 92b denotes a projecting part that is formed at the periphery of the opening on the laser irradiated surface 8b side (hereinafter referred to as "second projecting part").

As is evident from the figures, the air hole 9 formed by laser according to the first embodiment has the openings 91a and 91b which are approximately circular in shape, and the diameter x of the opening 91a on the laser non-irradiated surface 8a side of the second support 8 is smaller than the diameter y of the opening 91b on the laser irradiated surface 8b side. Further, in the air hole 9, since the second support 8 is thermally melted by laser irradiation, the resin of the second support 8 swells, resulting in the first and second projecting parts 92a and 92b at the peripheries of the openings 91a and 91b, respectively. In FIG. 3, ya indicates the height of the first projecting part 92a that is formed at the periphery of the opening 91a on the laser non-irradiated surface 8a side, and yb indicates the height of the second projecting part 92b that is formed at the periphery of the opening 91b on the laser non-irradiated surface 8b side.

Next, the functions and effects will be described.

Initially, the diameters of the openings 91a and 91b of the air hole according to the first embodiment will be described in detail.

Figure 4:
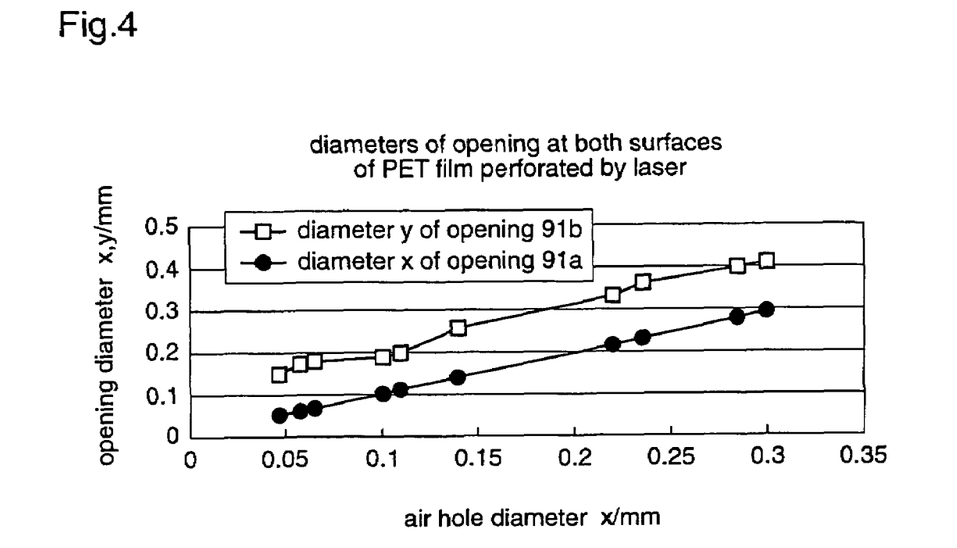
FIG. 4 is a graph illustrating change in the diameter of openings at the both surfaces of the second support, which are formed when air holes of various diameters are perforated in the second support using $CO_2$ laser, in the biosensor according to the first embodiment of the present invention.

FIG. 4 is a graph illustrating variations in the diameters x and y of the openings 91a and 91b which are formed on the both sides of the second support 8 when air holes of various sizes are perforated in the second support 8 comprising 0.1 mm thick polyethylene terephthalate, using SUNX $CO_2$ laser marker LP-211. In the following description, "air hole diameter" indicates the diameter x of the opening 91a which is formed on the laser non-irradiated surface 8a side of the air hole 9 that penetrates the second support 8.

As is evident from FIG. 4, regardless of the size of the air hole diameter x, the diameter y of the opening 91b on the $CO_2$ laser irradiated surface 8b side becomes larger than the diameter x of the opening 91a on the laser non-irradiated surface 8a side, and as shown in FIG. 3, the cross-section of the air hole 9 is of such trapezoidal shape that the diameter of the opening is tapered to be smaller from the laser irradiated surface 8b side toward the laser non-irradiated surface 8a side. The size of the air hole diameter x that can be perforated using $CO_2$ laser is desirably 0.05~0.30 mm when the productivity is considered (the diameter of the opening 91a on the laser non-irradiated surface 8a side is 0.05~0.30 mm, and the diameter of the opening 91b on the laser irradiated surface 8b side is 0.15~0.45 mm).

Tables 1(a) and 1(b) show the results of verifications for the bubbles remaining in the specimen supply path 7 due to differences in the size of the air hole diameter x when the specimen is drawn into the specimen supply path 7.

Because, as described above, the air hole 9 according to the first embodiment have different diameters for the openings 91b and 91a at the laser irradiated surface 8b and at the laser non-irradiated surface 8b, respectively, it is necessary to verify two patterns of bubbles remaining in the specimen supply path 7 in a case where the side facing the specimen supply path 7 is the laser irradiated surface 8b (Table 1(a)) and in a case where the side facing the specimen supply path 7 is the laser non-irradiated surface 8a (Table 1(b)).

Tables 1(a) and 1(b) show the results of verifications for the bubbles remaining in the specimen supply path 7 when air holes of various diameters x are perforated through the second support 8 comprising 0.1 mm thick polyethylene terephthalate, using SUNX $CO_2$ laser marker LP-211, and a control solution having a low viscosity of 25 mPas is supplied to the specimen supply path 7 having a size of 1.5 mm×3.4 mm×0.155 mm. Table 1(a) shows the result of verifications in the case where the laser irradiated surface 8b is placed facing the specimen supply path 7, and table 1(b) shows the result of verifications in the case where the laser non-irradiates surface 8a is placed facing the specimen supply path 7.

TABLE 1

(a) the case where the laser irradiated surface 8b faces the specimen supply path

| air hole diameter x[mm] | 0.05 | 0.1 | 0.15 | 0.2 | 0.25 | 0.3 |
|---|---|---|---|---|---|---|
| state in specimen supply path | ○ | ○ | ○ | ○ | ○ | ○ |

(b) the case where the laser non-irradiated surface 8a faces the specimen supply path

| air hole diameter x[mm] | 0.05 | 0.1 | 0.15 | 0.2 | 0.25 | 0.3 |
|---|---|---|---|---|---|---|
| state in specimen supply path | X | Δ | ○ | ○ | ○ | ○ |

○: no bubbles remain
Δ: minute amount of bubbles remain
X: large amount of bubbles remain As shown in Table 1(a), when the laser irradiated surface 8b is placed facing the specimen supply path 7, there remains no bubbles even if the air hole diameter x is as minute as 0.05~0.10 mm, and therefore, a sufficient amount of specimen can be drawn into the specimen supply path 7 even if the viscosity of the specimen is low. However, when the laser non-irradiated surface 8a is placed facing the specimen supply path 7 as shown in FIG. 1(b), the air hole diameter x as minute as 0.05~0.1 mm causes bubbles to remain, and therefore a sufficient amount specimen cannot be drawn into the specimen supply path 7 when the viscosity of the specimen is low.

Therefore, it is desired that the size of the air hole 9 penetrating through the second support 8 should be 0.05 mm~0.30 mm, that is, the diameter x of the opening 91a formed at the laser non-irradiated surface 8a should be 0.05 mm~0.30 mm (in terms of area, $1.96 \times 10^{-3}$~$7.07 \times 10^{-2}$ $mm^2$) and the diameter y of the opening 91b formed at the laser irradiated surface 8b should be 0.15 mm~0.45 mm (in terms of area, $1.76 \times 10^{-2}$~$1.58 \times 10^{-1}$ $mm^2$). More preferably, it is desired that, with the $CO_2$ laser irradiated surface 8b facing the specimen supply path 7, the air hole diameter x should be at least 0.05 mm~0.10 mm, that is, the diameter x of the opening 91a formed at the laser non-irradiated surface 8a should be 0.05 mm~0.10 mm (in terms of area, $1.96 \times 10^{-3}$~$7.85 \times 10^{-3}$ $mm^2$) and the diameter y of the opening 91b formed at the laser irradiated surface 8b should be 0.15 mm~0.20 mm (in terms of area, $1.76 \times 10^{-2}$~$3.14 \times 10^{-2}$ $mm^2$).

When the air hole 9 has the openings as mentioned above, releasing of air from the specimen supply path 7 of the biosensor 100 is promoted even if the diameter of the air hole 9 is minute, so that no bubbles remain in the specimen supply path 7. Therefore, an amount of specimen that is sufficient for obtaining measurement results of substrates included in the specimen can be drawn into the specimen supply path 7 through the minute air hole 9, thereby to obtain highly accurate measurement result.

Further, when the $CO_2$ laser irradiated surface 8b of the second support 8 is placed facing the specimen supply path 7 as described above, an amount of specimen that is sufficient for obtaining a measurement result of substrates included in the specimen can be drawn into the specimen supply path 7 through a more minute air hole 9.

Next, a description will be given of the first and second projecting parts 92a and 92b which are formed at the peripheries of the openings 91a and 91b of the air hole 9, respectively.

Figure 5:
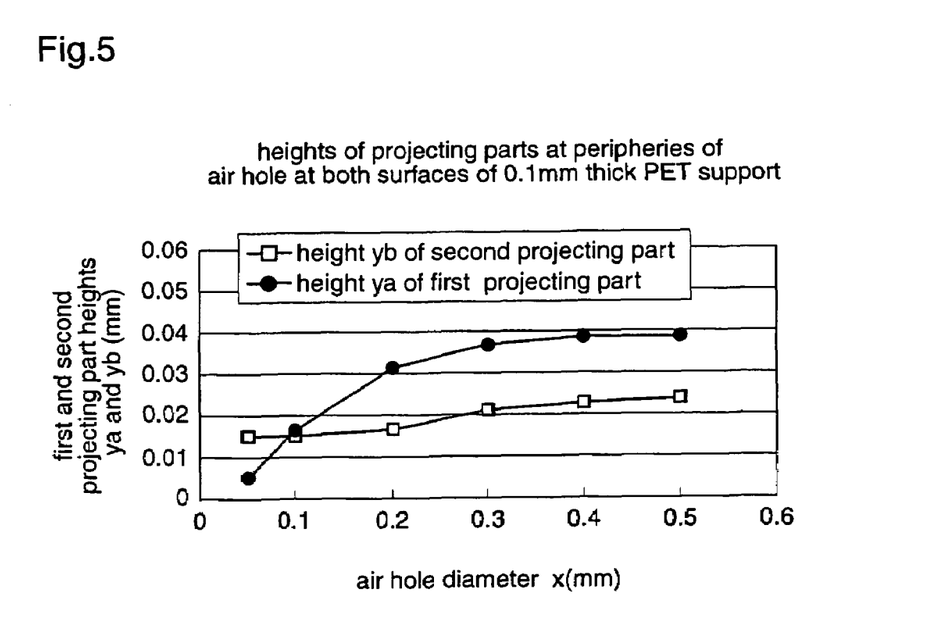
FIG. 5 is a graph illustrating change in the heights ya and yb of projecting portions in the vicinity of the openings at the both surfaces of the second support, which are formed when air holes of various diameters are perforated in the second support using $CO_2$ laser, in the biosensor according to the first embodiment of the present invention.

FIG. 5 shows a graph illustrating variations in the heights ya and yb of the first and second projecting parts 92a and 92b at the peripheries of the openings 91a and 91b which are formed at the both sides of the second support 2, when air holes of various diameters x are formed through the second support 8 comprising 0.1 mm thick polyethylene terephthalate, using SUNX $CO_2$ laser marker LP-211.

As is evident from FIG. 5, the height yb of the second projecting part 92b that is formed at the periphery of the opening 91b on the laser irradiated surface 8b side is kept approximately constant even if the air hole diameter x varies in a range of 0.05~0.5 mm. On the other hand, the height ya of the first projecting part 92a that is formed at the periphery of the opening 91a on the laser non-irradiated surface 8a side varies drastically in the range of the air hole diameter x being 0.05~0.3 mm, and is kept approximately constant when the air hole diameter x exceeds 0.3 mm. To be specific, when the thickness of the second support 8 is 1.0 mm, the height yb of the second projecting part 92b is 0.015~0.025 mm and the height ya of the first projecting part 92a is 0.005~0.040 mm.

Table 2 shows the result of verification for the relationship between the heights (air hole diameters) of the projecting parts and the state of overflow of the specimen from the air hole when the specimen is drawn into the detection supply path 7. In Table 2, the biosensor is placed with the laser irradiated surface 8b of the second support 8 facing the specimen supply path 7.

Table 2 shows the result of verifications as to whether, when air holes of various diameters x (0.05~0.5 mm) are formed through the second support 8 comprising 0.1 mm thick polyethylene terephthalate, using SUNX $CO_2$ laser marker LP-211, and a control solution having a low viscosity of 25 mPas is supplied to the specimen supply path 7 having a size of 1.5 mm×3.4 mm×0.155 mm, the control solution flows over the periphery of the air hole (in this case, the opening 91a).

In table 2, in order to verify how much the overflow of the control solution from the opening 91a differs between the case where the projecting part exists at the periphery of the air hole and the case where no projecting part exists, the case where the air hole 9 is perforated by press working resulting in no projecting part and the case where the air hole 9 is perforated by laser processing resulting in a projection part are compared. Further, in order to verify as to whether the overflow differs or not between the case where water-repellent finishing is done and the case where no water-repellent finishing is done, a biosensor in which the periphery of the air hole 9 having the projecting part, (which are respectively formed by the above-mentioned respective perforating methods,) is subjected to water-repellent finishing and a biosensor in which the periphery of the air hole 9 having no projecting part is subjected to water-repellent finishing, (which are respectively formed by the above-mentioned respective perforating methods,) are compared with each other.

the specimen supply path 7. As a result, highly accurate measurement result can be obtained in the biosensor 100.

Further, according to the first embodiment, the second substrate 8 is thermally melted by irradiating the same with $CO_2$ laser to perforate the air hole 9, thereby producing the projecting parts 92a and 92b at the peripheries of the openings 91a and 91b on the both surfaces 8a and 8b of the second support 8, respectively. Therefore, even if water-repellent finishing onto the second support 8, which has conventionally been needed, is omitted from the biosensor fabrication process, overflow of the specimen from the air hole 9 can be prevented. As a result, a biosensor that provides a highly accurate measurement result can be realized at low costs. Further, in contrast to the conventional press working, no punching residues occur, resulting in reduction in industrial waste.

TABLE 2

| perforation method | water-repellent finish | air hole diameter [mm] | | | | | | | | | |
|---|---|---|---|---|---|---|---|---|---|---|---|
| | | 0.05 | 0.1 | 0.15 | 0.2 | 0.25 | 0.3 | 0.35 | 0.4 | 0.45 | 0.5 |
| press (no projection) | yes | — | — | — | — | — | ○ | ○ | ○ | ○ | ○ |
| | no | — | — | — | — | — | X | X | X | X | X |
| laser (projection) | yes | ○ | ○ | ○ | ○ | ○ | ○ | ○ | ○ | ○ | ○ |
| | no | ○ | ○ | ○ | ○ | ○ | ○ | ○ | ○ | ○ | ○ |

○: no overflow
X: overflow occurs
—: unproducible

As shown in Table 2, when the periphery of the air hole 9 is subjected to water-repellent finishing, no control solution flows over the air hole 9, even when the air hole 9 is formed by press working, i.e., even when there is no projecting part at the periphery of the air hole. However, the control solution undesirably flows over the air hole 9 when there is no projecting part at the periphery of the air hole 9 and the periphery of the air hole 9 is not subjected to water-repellent finishing. The reason is because, in the air hole 49 perforated by the conventional press working, the peripheries of the openings produced in the second support 48 are flat as shown in FIGS. 7(a) and 7(b).

On the other hand, when the air hole 9 is formed by laser processing as in the first embodiment, i.e., when there are projecting parts at the peripheries of the air hole, no control solution flows over the air hole 9 regardless of whether the periphery of the air hole is subjected to water-repellent finishing or not as well as regardless of the size of the air hole diameter x.

Therefore, in the case where the second support 8 comprising the above-mentioned material and having the above-mentioned thickness is employed, when the diameter x of the air hole 9 penetrating through the second support 8 is 0.05~0.5 mm (in terms of area, $1.96 \times 10^{-3} \sim 7.07 \times 10^{-2}$ mm$^2$) and the height ya of the first projecting part 92a at the periphery of the opening 91a is 0.005~0.04 mm, overflow of the specimen can be prevented by the projecting part 92a produced at the periphery of the opening 91a when a specimen having a very low viscosity is drawn into the specimen supply path 7 of the biosensor 100 even if the surface of the second support 8 is not subjected to water repellent finishing.

As described above, according to the first embodiment, a minute air hole 9 having a diameter that is tapered smaller from the laser irradiated surface 8b to the laser non-irradiated surface 8a is perforated in the second support 8 of the biosensor 100 by thermally melting the second support 8 from one surface side to the other surface side using $CO_2$ laser, and the $CO_2$ laser irradiated surface 8b of the second support 8 in which the air hole 9 is formed, is placed facing the specimen supply path 7. Therefore, even if the air hole 9 of the biosensor 100 is a minute hole, occurrence of bubbles can be prevented and thereby an amount of specimen that is sufficient for obtaining measurement results of substrates included in the specimen can be drawn into the specimen supply path 7, regardless of the viscosity of the specimen to be supplied to Furthermore, according to the first embodiment, the laser non-irradiated surface 8a having the smaller diameter of the opening of the air hole 9 that is perforated in the second support 8 is the outer surface of the biosensor 100. Therefore, even when the user drops the specimen on the air hole 9 by mistake, the specimen is hardly drawn into the specimen supply path 7, thereby avoiding incorrect measurement results.

Further, since the second support 8 is placed as mentioned above, the second projecting part 92b having the smaller height is placed facing the specimen supply path 7, whereby the second projecting part 92b never blocks the flow of the specimen and the pathway of bubbles included in the specimen, and consequently, occurrence of bubbles in the specimen supply path 7 can be prevented regardless of the viscosity of the specimen supplied to the specimen supply path 7, resulting in more accurate measurement result.

While in this first embodiment the air hole 9 is perforated using a $CO_2$ laser device, the air hole 9 may be formed using another laser device or the like.

Further, the method of forming the air hole 9 is not restricted to the laser processing as long as a minute air hole having a diameter that is tapered smaller from one surface toward the other surface can be perforated as shown in FIG. 2. For example, the air hole 9 may be formed by puncturing the second support with a heated needle having a pointed tip. However, only laser irradiation can realize perforation processing that makes the air hole with a diameter x of 0.05 mm.

Further, while in the first embodiment the shape of the opening 91a, 91b of the air hole 9 is nearly circle, it may be any of ellipse, line having a very small width, triangle, square, rectangle, polygon, and the like.

The biosensor according to the present invention is useful as a biosensor for analyzing of a specimen having viscosity that varies among individuals, such as blood, because the biosensor can provide a correct response value without depending on the viscosity of the specimen. Further, in the biosensor according to the present invention, due to that the air hole is processed by melting using laser, cost reduction can be achieved, as well as occurrence of punching residues can be avoided in contrast to the conventional press working, thereby also resulting in reduction in industrial waste.

What is claimed is:

1. A biosensor comprising:
first and second supports bonded together to form a space between the supports as a specimen supply path, the space between the supports having a specimen-drawing opening to outside the biosensor through which a supplied specimen is drawn into the space between the supports so as to react with a reagent disposed in the specimen supply path;
an air hole formed in the second support and leading from the specimen supply path to the outside of the biosensor, a diameter of an opening of the air hole at one surface of the second support which faces the specimen supply path being larger than a diameter of an opening of the air hole at the other surface of the second support, the air hole being located at a position different from the position of the specimen-drawing opening of the space between the supports so as to accelerate the drawing of the specimen into the space between the supports,
wherein
the area of the opening of the air hole at the one surface of the second support facing the specimen supply path is $1.76 \times 10^{-2} \sim 3.14 \times 10^{-2}$ mm$^2$, and
the area of the opening at the other surface of the second support is $1.96 \times 10^{-3} \sim 7.85 \times 10^{-3}$ mm$^2$.

2. A biosensor as defined in claim 1 wherein
the shape of the opening of the air hole is any of circle, ellipse, line having a very small width, triangle, square, rectangle, and polygon.

3. A biosensor comprising:
first and second supports bonded together to form a space between the supports as a specimen supply path, the space between the supports having a specimen-drawing opening to outside the biosensor through which a supplied specimen is drawn into the space between the supports so as to react with a reagent disposed in the specimen supply path;
an air hole formed in the second support and leading from the specimen supply path to the outside of the biosensor, a diameter of an opening of the air hole at one surface of the second support which faces the specimen supply path being larger than a diameter of an opening of the air hole at the other surface of the second support, the air hole being located at a position different from the position of the specimen-drawing opening of the space between the supports so as to accelerate the drawing of the specimen into the space between the supports,
wherein
the openings of the air hole are nearly circular in shape, and
the diameter of the opening of the air hole at the one surface of the second support facing the specimen supply path is 0.15~0.20 mm, and the diameter of the opening of the air hole at the other surface of the second support is 0.05~0.10 mm.

4. A biosensor as defined in claim 3 wherein
the shape of the opening of the air hole is any of circle, ellipse, line having a very small width, triangle, square, rectangle, and polygon.

5. A biosensor comprising:
first and second supports bonded together to form a space between the supports as a specimen supply path, the space between the supports having a specimen-drawing opening to outside the biosensor through which a supplied specimen is drawn into the space between the supports so as to react with a reagent disposed in the specimen supply path;
an air hole formed in the second support and leading from the specimen supply path to the outside of the biosensor, a diameter of an opening of the air hole at one surface of the second support which faces the specimen supply path being larger than a diameter of an opening of the air hole at the other surface of the second support, the air hole being located at a position different from the position of the specimen-drawing opening of the space between the supports so as to accelerate the drawing of the specimen into the space between the supports,
wherein
said air hole has a first projecting part that is formed on the periphery of the opening of the air hole at the other surface of the second support, and a second projecting part that is formed on the periphery of the opening of the air hole at the one surface of the second support facing the specimen supply path.

6. A biosensor as defined in claim 5 wherein
when the thickness of the second support is 0.01 mm ~0.5 mm and the area of the opening of the air hole at the other surface of the second support is $1.96 \times 10^{-3} \sim 7.85 \times 10^{-3}$ mm$^2$, the heights of the first and second projecting parts are 0.005~0.04 mm.

7. A biosensor as defined in claim 5 wherein
the height of the first projecting part is larger than the height of the second projecting part.

8. A biosensor as defined in claim 5 wherein
the shape of the opening of the air hole is any of circle, ellipse, line having a very small width, triangle, square, rectangle, and polygon.

9. A biosensor comprising:
first and second supports bonded together to form a space between the supports as a specimen supply path, the space between the supports having a specimen-drawing opening to outside the biosensor through which a supplied specimen is drawn into the space between the supports so as to react with a reagent disposed in the specimen supply path;
an air hole formed in the second support and leading from the specimen supply path to the outside of the biosensor, a diameter of an opening of the air hole at one surface of the second support which faces the specimen supply path being larger than a diameter of an opening of the air hole at the other surface of the second support, the air hole being located at a position different from the position of the specimen-drawing opening of the space between the supports so as to accelerate the drawing of the specimen into the space between the supports,
wherein
the area of the opening of the air hole at the one surface of the second support facing the specimen supply path is $1.76 \times 10^{-2} \sim 1.58 \times 10^{-1}$ mm$^2$, and
the area of the opening of the air hole at the other surface of the second support is $1.96 \times 10^{-3} \sim 7.07 \times 10^{-2}$ mm$^2$.

10. A biosensor as defined in claim 9 wherein
the shape of the opening of the air hole is any of circle, ellipse, line having a very small width, triangle, square, rectangle, and polygon.

11. A biosensor comprising:

first and second supports bonded together to form a space between the supports as a specimen supply path, the space between the supports having a specimen-drawing opening to outside the biosensor through which a supplied specimen is drawn into the space between the supports so as to react with a reagent disposed in the specimen supply path;

an air hole formed in the second support and leading from the specimen supply path to the outside of the biosensor, a diameter of an opening of the air hole at one surface of the second support which faces the specimen supply path being larger than a diameter of an opening of the air hole at the other surface of the second support, the air hole being located at a position different from the position of the specimen-drawing opening of the space between the supports so as to accelerate the drawing of the specimen into the space between the supports, wherein the openings of the air hole are nearly circular in shape, and the diameter of the opening of the air hole at the one surface of the second support facing the specimen supply path is 0.150~0.45 mm, and the diameter of the opening of the air hole at the other surface of the second support is 0.05~0.30 mm.

12. A biosensor as defined in claim 11 wherein the shape of the opening of the air hole is any of circle, ellipse, line having a very small width, triangle, square, rectangle, and polygon.

* * * * *